(12) United States Patent
Dejanovic et al.

(10) Patent No.: US 7,315,281 B2
(45) Date of Patent: Jan. 1, 2008

(54) LOCATION DETERMINATION METHOD AND SYSTEM FOR ASSET TRACKING DEVICES

(75) Inventors: Thomas Dejanovic, Croydon (AU); John S. Gloekler, Oakland, CA (US); Geoffrey J. Smith, Brisbane (AU); Philip J. Ryan, Stanmore (AU); John O'Sullivan, Hunters Hill (AU)

(73) Assignee: G2 Microsystems Pty. Ltd., Haymarket (AU)

( * ) Notice: Subject to any disclaimer, the term of this patent is extended or adjusted under 35 U.S.C. 154(b) by 0 days.

(21) Appl. No.: 11/194,116

(22) Filed: Jul. 30, 2005

(65) Prior Publication Data

US 2006/0125694 A1   Jun. 15, 2006

Related U.S. Application Data (60) Provisional application No. 60/592,840, filed on Jul. 30, 2004.

(51) Int. Cl.
*G01S 3/02* (2006.01)
(52) U.S. Cl. ........................ 342/463; 342/457
(58) Field of Classification Search ................ 342/451, 342/457, 463–465; 455/456.1, 456.3, 457
See application file for complete search history.

(56) References Cited

U.S. PATENT DOCUMENTS

| | | | |
|---|---|---|---|
| 5,774,876 A | 6/1998 | Woolley et al. | |
| 6,400,272 B1 | 6/2002 | Holtzman et al. | |
| 6,504,503 B1 | 1/2003 | Saint-Hilaire et al. | |
| 6,509,828 B2 | 1/2003 | Bolavage et al. | |
| 6,539,281 B2 | 3/2003 | Wan et al. | |
| 6,614,351 B2 | 9/2003 | Mann et al. | |
| 6,624,752 B2 | 9/2003 | Klitsgaard et al. | |
| 6,687,609 B2 | 2/2004 | Hsiao et al. | |
| 6,700,533 B1 | 3/2004 | Werb et al. | |
| 6,745,027 B2 | 6/2004 | Twitchell, Jr. | |
| 6,804,578 B1 | 10/2004 | Ghaffari | |
| 6,853,294 B1 | 2/2005 | Ramamurthy et al. | |
| 6,859,761 B2 | 2/2005 | Bensky et al. | |
| 6,892,054 B2 | 5/2005 | Belcher et al. | |

(Continued)

FOREIGN PATENT DOCUMENTS

WO  WO 01/79988  10/2001

(Continued)

OTHER PUBLICATIONS

PCT Search Report, PCT/US04/43896, Dec. 30, 2004, G2 Microsystems PTY LTD.

*Primary Examiner*—Dao Phan
(74) *Attorney, Agent, or Firm*—Blakely Sokoloff Taylor & Zafman LLP (57) ABSTRACT

A method of determining a geographical location of an asset tracking device, includes searching, by the asset tracking device, for available location determination schemes at the geographical location, selecting one of the available location determination schemes, and determining coordinates of the geographical location using the selected location determination scheme. Some embodiments also include making a decision based, at least in part, upon the geographical location coordinates determined by using the selected location determination scheme. Some embodiments include transmitting a location message, the location message including the coordinates of the geographical location and an indication as to the selected location determination scheme.

22 Claims, 6 Drawing Sheets

U.S. PATENT DOCUMENTS

| | | |
|---|---|---|
| 6,933,849 B2 | 8/2005 | Sawyer |
| 6,934,540 B2 | 8/2005 | Twitchell, Jr. |
| 6,963,289 B2 | 11/2005 | Aljadeff et al. |
| 6,968,194 B2 | 11/2005 | Aljadeff et al. |
| 6,978,118 B2 | 12/2005 | Vesikivi et al. |
| 2002/0078363 A1 | 6/2002 | Hill et al. |
| 2003/0225515 A1* | 12/2003 | Havlark et al. ............. 701/213 |
| 2003/0232598 A1 | 12/2003 | Aljadeff et al. |
| 2004/0024644 A1 | 2/2004 | Gui et al. |
| 2004/0024658 A1 | 2/2004 | Carbone et al. |
| 2004/0024660 A1 | 2/2004 | Ganesh et al. |
| 2004/0061646 A1* | 4/2004 | Andrews et al. ............ 342/463 |
| 2004/0072577 A1 | 4/2004 | Myllymaki et al. |
| 2004/0100379 A1 | 5/2004 | Boman et al. |
| 2004/0203870 A1 | 10/2004 | Aljadeff et al. |
| 2004/0227630 A1 | 11/2004 | Shannon et al. |
| 2005/0128139 A1 | 6/2005 | Misikangas et al. |
| 2005/0131635 A1 | 6/2005 | Myllymaki et al. |
| 2005/0136845 A1* | 6/2005 | Masuoka et al. ........ 455/67.14 |
| 2005/0156711 A1 | 7/2005 | Aljadeff et al. |
| 2005/0181804 A1 | 8/2005 | Misikangas et al. |
| 2005/0197139 A1 | 9/2005 | Misikangas et al. |
| 2005/0207381 A1 | 9/2005 | Aljadeff et al. |
| 2005/0228860 A1* | 10/2005 | Hamynen et al. ........... 709/203 |
| 2006/0052115 A1* | 3/2006 | Khushu ................... 455/456.3 |
| 2006/0119471 A1 | 6/2006 | Rudolph et al. |

FOREIGN PATENT DOCUMENTS

| | | |
|---|---|---|
| WO | WO 03/032501 | 4/2003 |
| WO | WO 2004/006051 | 1/2004 |
| WO | WO 2004/013731 | 2/2004 |
| WO | WO 2004/074965 | 9/2004 |

* cited by examiner

LOCATION DETERMINATION METHOD AND SYSTEM FOR ASSET TRACKING DEVICES

RELATED APPLICATIONS

This application claims the benefit of previously filed U.S. provisional application 60/592,840 filed 30 Jul. 2004, the entirety of which is hereby incorporated by reference.

FIELD OF THE INVENTION

The invention relates to method and system for geographically locating an asset tracking device located on an asset. In particular, although not exclusively, the invention relates to a method and system for geographically locating an asset tracking device located on an asset and reporting this geographical location in a transparent and consistent manner.

BACKGROUND TO THE INVENTION

A major focus of companies today is the security and visibility of management, processing or delivery of high value asset is outsourced to another company. The use of Radio Frequency Identification (RFID) tags to facilitate item tracking is well known.

RFID tags are electronic devices that generally comprise a passive transponder and an integrated circuit programmed with unique identification information. In the context of a supply chain they are located on items and pallets of the items and may be used as a replacement for barcodes to identify items.

An RFID tag reader is used to read the unique data programmed on the RFID tag. An RFID tag reader is comprised of an antenna, a transceiver and a decoder can be configured either as a handheld unit or a fixed-mount device. The reader emits radio waves in ranges of anywhere from a few centimeters to about 40 meters, depending on the readers power output and the radio frequency used. When an RFID tag passes through the reader's electromagnetic zone, it detects the reader's activation signal. This signal energizes the RFID tag and enables the tag to transmit data, which is encoded on its integrated circuit, to the reader. The reader decodes this data, which may be passed to a host computer for processing.

RFID tags are generally passive tags, as discussed above, in that they have no internal power source and rely on an external source to provide power. In some instances, RFID tags may be active, in that they have an internal power source. Active RFID tags are more expensive and bulkier than passive RFID tags and, as such, are generally not the preferred tracking device for item level tracking.

Due to memory and processor limitations, the data stored on RFID tags is generally little more than a unique identifier for the item. Conventional systems offer little more than an electronic bar code that can be read from moderate distances.

A further disadvantage of prior art RFID tracking system is the lack of synchronicity and integrity of data across an entire supply chain. As different entities become involved in subsequent phases of the supply chain, the effective tracking of items from source to destination becomes complex and expensive. The integration of a company's backend systems with transport contractors and the like to enable auditing and tracking of the company's items throughout the supply chain is difficult and not scaleable.

For example consider the situation where a transport contractor is used by a wide variety of companies to move freight. Each company has their own RFID system, while the transport contractor has its own RFID system. While the transport company can read the data on the RFID tags for each company, the integration of the transport contractor's backend computer system with that of each company is more difficult and expensive, and hence the companies have difficult in reliably tracking their products throughout the supply chain.

More sophisticated tags have been developed whereby these tags have wireless communication capabilities, position determination capabilities, and environmental sensing capabilities. These tags are able to send geographical location schemes known in the art that a sophisticated tag may employ to determine its geographical location. These include standard GPS positioning, and a range of location specific radio location methods that rely on the sophisticated tag interacting with local reference entities that have a known position. The sophisticated tag interacts with the local location technology that is supported, or the GPS system, in order to communicate its geographical location to the supplier.

However, different locations throughout the supply chain employ different location determination schemes. Furthermore, GPS can be unreliable when used in an indoor location or when the GPS satellite signals are obscured such as in a warehouse or within a shipping container. As such, a significant difficulty that suppliers encounter when trying to reliably track an asset through the supply chain is that the asset may pass through locations that support varying location determination schemes and hence it may not be possible for the sophisticated tag to determine its geographical location at all locations throughout the supply chain.

What is needed is a sophisticated tag that has the capability to reliably determine its geographical location at all points throughout the supply chain.

SUMMARY OF THE INVENTION

Briefly, a method of determining a geographical location of an asset tracking device, includes searching, by the asset tracking device, for available location determination schemes at the geographical location, selecting one of the available location determination schemes, and determining coordinates of the geographical location using the selected location determination scheme. Some embodiments also include making a decision based, at least in part, upon the geographical location coordinates determined by using the selected location determination scheme. Some embodiments include transmitting a location message, the location message including the coordinates of the geographical location and an indication as to the selected location determination scheme.

DETAILED DESCRIPTION

Generally, the present invention provides methods and systems for determining the location of asset tracking devices when GPS signals are obstructed by determining which one or more local location determination schemes are available, selecting at least one of the local location determination schemes, and communicating with a plurality of the reference tags of the selected local location determination scheme, those reference tags having known locations, and finally determining the distances of the asset tracking from each of several reference tags, and from that information computing the actual location of the asset tracking device.

In one form, although it needs not to be the only or indeed the broadest form, the invention includes:

searching for available location determination schemes available at the geographical location;

selecting one of the available location determination schemes;

determining co-ordinates of the geographical location using the selected location determination scheme; and communicating a location message to a tracking entity, the location message including the coordinates of the geographical location and an indication as to the selected location determination scheme.

Reference herein to "one embodiment", "an embodiment", "some embodiments", or similar formulations, means that a particular feature, structure, operation, or characteristic described in connection with the embodiment, is included in at least one embodiment of the present invention. Thus, the appearances of such phrases or formulations herein are not necessarily all referring to the same embodiment. Furthermore, various particular features, structures, operations, or characteristics may be combined in any suitable-manner in one or more embodiments.

Figure 1:
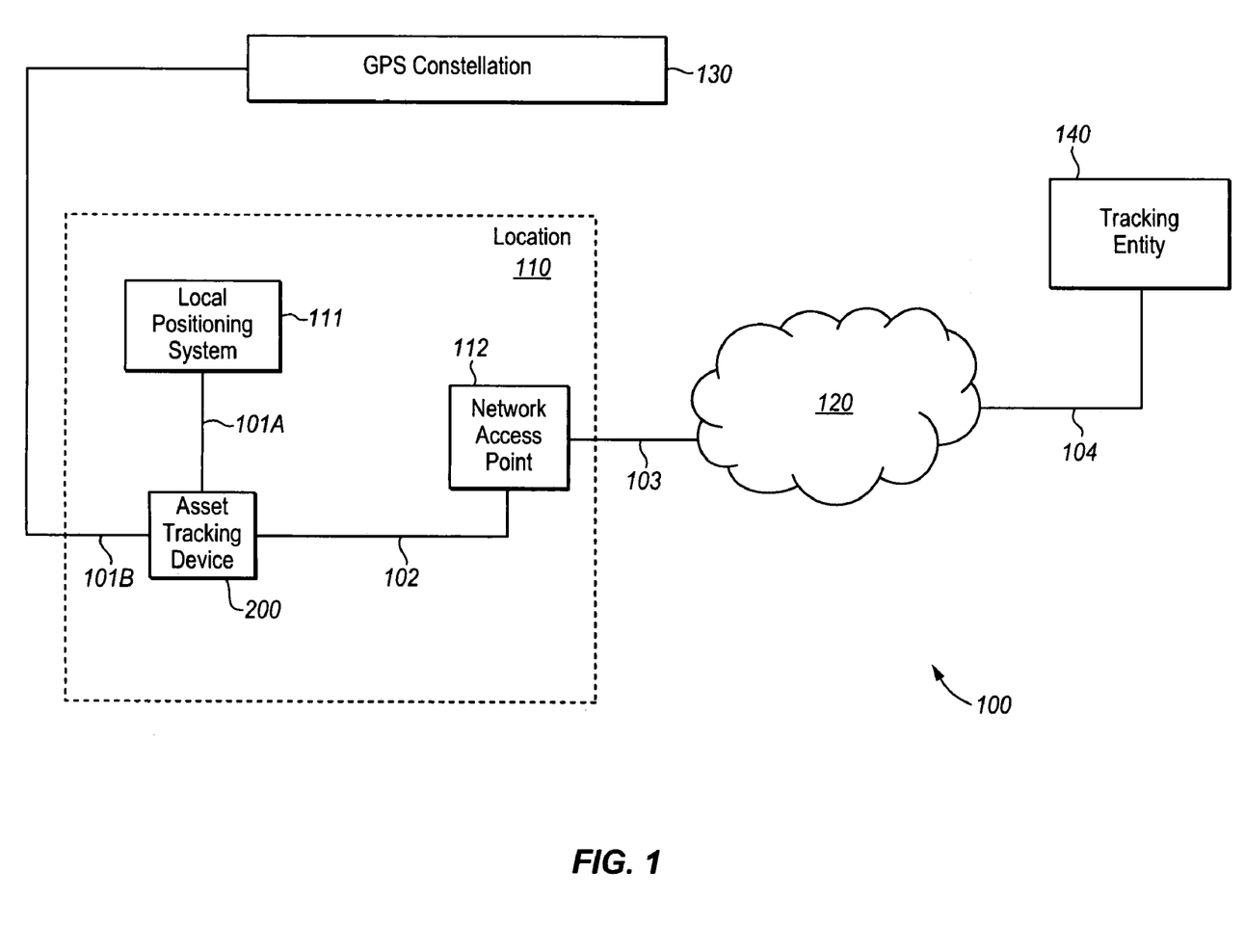
FIG. 1 is high-level block diagram of a location system in accordance with the present invention.

FIG. 1 shows a conceptual block diagram of a location system 100 according to an embodiment of the present invention. System 100 comprises a location 110, a public network in the form of the Internet 120, a tracking entity 140 and GPS constellation 130.

In this illustrative embodiment, location 110 is warehouse that is geographically separated from tracking entity 140. It is noted that location 110 may alternatively be a container ship, a shipping container, a truck or a similar such location through which a asset may be moved through in a supply chain environment. Location 110 comprises an asset tracking device 200, local positioning system 111, and a network access point 112.

Asset tracking device 200 is located on an asset to be tracked (not shown). Asset tracking device 200 is in communication with network access point 112 via communication pathway 102. In this illustrative embodiment, network access point 200 is in the form of a wireless access point as is known in the art. Communication between asset tracking device 200 and network access point 112 is via wireless communication with Internet 120 via communication pathway 103 as is known in the art.

Asset tracking device 200 is in communication with GPS constellation 130 via communication pathway 101B. It will be appreciated that GPS constellation 130 is formed from a plurality of GPS satellites which transmit GPS data used by GPS receivers to determine position coordinates of the receiver. In this embodiment, asset tracking device 200 has the capability to determine its location using GPS constellation 130.

Additionally, asset tracking device 200 is in communication with local positioning system 111 via wireless communication pathway 101A. Local positioning system 111 provides for a mechanism whereby asset tracking device 200 can determine its geographical location using a wireless communication protocol. Local positioning system 111 may support a Received Signal Strength Indicator (RSSI) scheme, a direction of arrival of a wireless communication signal scheme, a time of arrival of a wireless communication signal scheme, time difference of arrival of a wireless communication signal scheme, or any other form of location-determination scheme using a wireless communication protocol. Various embodiments of location determination schemes which are supported by local positioning system 111 are discussed below.

Tracking entity 140 is in communication with Internet 120 via communication pathway 104. This allows tracking entity 140 to be in operative communication with asset tracking device 200. Tracking entity 140 has an interest in communicating with asset tracking device 200 in order that tracking entity 140 may receive location messages from asset tracking device 200.

Figure 2:
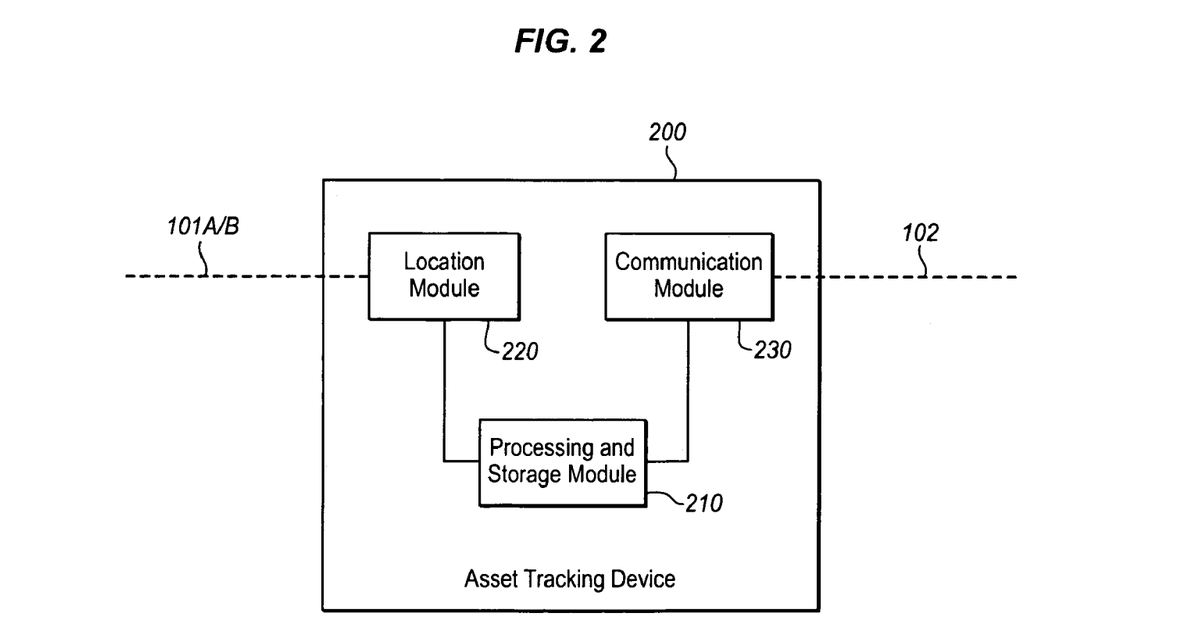
FIG. 2 is a block diagram of an asset tracking device forming part of the location system shown in FIG. 1.

FIG. 2 shows a high-level block diagram of asset tracking device 200. Asset tracking device 200 has a processing and storage module 210, a location module 220 and communication module 230. Communication module 230 is in wireless communication with network access point 112 via communication pathway 102 as previously discussed. In some embodiments, communication on communication pathway 102 adheres to the 802.11x suite of wireless communication protocols. Alternatively, other wireless communication protocols may be used. Additionally, communication module 230 is in communication with processing and storage module 210 of asset tracking device 200 as shown in FIG. 2.

Location module 220 is in communication with GPS constellation 130 is in communication pathway 101B. Additionally location module 220 is in communication with processing and storage module 210 of asset tracking device 200. Location module 220 is able to determine the geographical location of asset tracking device 200 using GPS constellation 130 as is known in the art.

Alternatively, In situations where signals from GPS constellation 130 are obscured, location module 220 is in communication with local positioning system 111 via communication pathway 101A. Communication pathway 101A is a wireless communication pathway and preferably complies with the 802.11x suite of wireless communication protocols. Hence, signals received on communication pathway 101A will be received by communication module 112 before being communicated to location module 220 to perform location determination calculations. In an alternative embodiment, location module 220 may form part of communication module 230.

The present invention enables asset tracking device 200 to calculate its geographical location and communicate this data to tracking entity 140 in a versatile and consistent manner. The invention enables asset tracking device 200 to determine its geographical location in situations where location signals from GPS constellation 130 are not receivable due to signal obstructions and the like. Furthermore, the present invention enables asset tracking device 200 to determine its geographical location at various locations 110 whereby the locations support differing local positioning systems 111.

Figure 3:
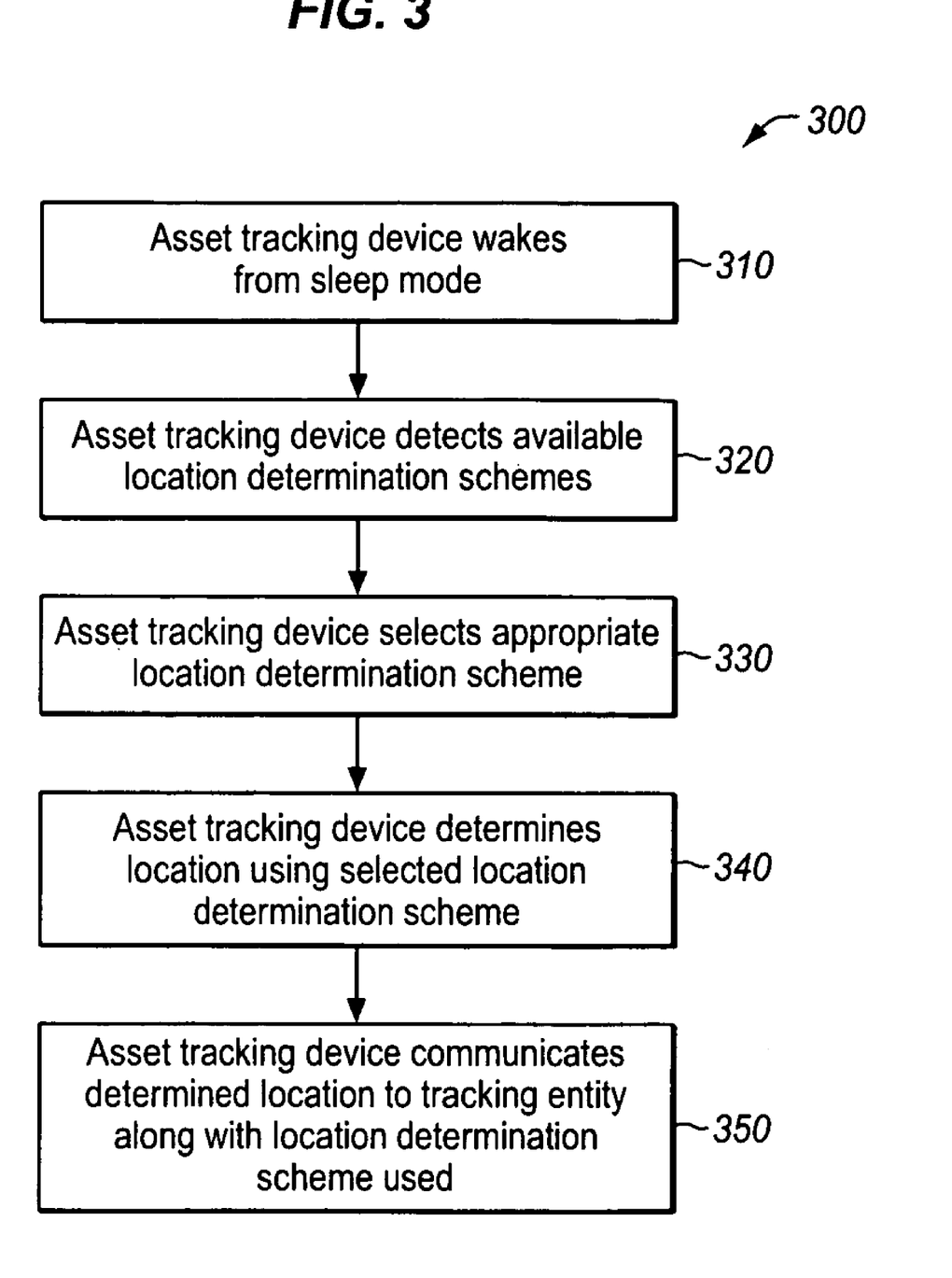
FIG. 3 is a flow diagram of a method for determining a geographical location of the asset tracking device shown in FIG. 2.

FIG. 3 illustrates a method 300, in accordance with the present invention, of determining a geographical location of asset tracking device 200. The method commences with asset tracking device 200 moving from a sleep to a wake mode, or state, (310). In order to save power, asset tracking device 200 generally exists in a sleep mode and moves to wake mode at predetermined intervals. These predetermined intervals are stored in processing and storage module 210. Alternatively, asset tracking device 200 may move to wake mode in response to a location request message received from tracking entity 140 at communication module 230.

Asset tracking device 200 then searches for location determination schemes available at location 110 (320). In some embodiments, asset tracking device searches for all location determination schemes that are available. Alternatively, asset tracking device 200 searches for location determination schemes in a predetermined order. For example, if no GPS signals are able to be received by location module 220, or if the signal strength of the GPS signal is below a predetermined threshold, then asset tracking device 200 interprets this to mean that location determination by way of GPS is not available, and searching for local location determination schemes supported by location 110 should be performed. It will be appreciated that in some embodiments, asset tracking device 200 is not equipped with a GPS receiver, and in such instances, asset tracking device relies upon local positioning system 111 to determine its location coordinates.

Similarly, asset tracking device 200 will search for signals that are characteristic of location determination schemes supported by local location positioning system 111. The characteristics of these local location determination schemes are described below.

Asset tracking device 200 then selects an appropriate location determination scheme (330) from the available location determination schemes. When all location determination schemes that are supported by asset tracking device 220 are searched, and there exists more than one available location determination scheme, the asset tracking device then selects the most appropriate location determination scheme based on certain criteria. Criteria that may be used to select the most appropriate location determination scheme include the known accuracy of the available location schemes, the time required to determine the coordinates of the asset tracking device using the available location schemes, the power requirements necessary to determine the coordinates of the asset tracking device using the various location schemes, and so on.

Asset tracking device 200 then determines the coordinates of its location (340) using the selected location determination scheme.

After the coordinates of the location have been determined, the asset tracking device assembles a location message which includes at least the location coordinates determined at 340 and an indication of the location scheme used to determine these coordinates. The location message may be communicated to tracking entity 140 (350).

Alternatively, more than one location determination scheme may be used by asset tracking device 200 to determine the coordinates of its geographical location and these details may be communicated in location messages to tracking entity 140.

Provided below is a discussion relating to embodiments of location determination schemes which local positioning system 111 of location 110 may support. As previously mentioned, GPS data from GPS constellation may be obstructed and hence it is desirable to have a local location determination system 111.

The location accuracy outdoors using GPS signals is typically of order 5-10 m. For situations where the GPS signals are obstructed, a replacement system of some form is needed. These local location determination schemes employ similar characteristics and are supported by a local positioning system 111 that utilizes reference entitles that have known coordinates and the ability to transmit these known coordinates over a wireless communication pathway. In some embodiments, this wireless communication pathway complies with the 802.11x suite of wireless communication protocols.

Three of the known local location determination schemes are signal strength, direction of arrival, and time of arrival. The characteristics of these location determination schemes and the method of determining the coordinates of a location using each scheme are described below.

In one embodiment, local positioning system 111 utilizes the received signal strength of a communication from a reference entity to infer the approximate distance from an asset tracking device 200 to two or more reference entities.

The indoor propagation characteristics at 2.4 GHz are determined by shadowing and loss through obstacles, diffraction around obstacles and reflections off objects so that the overall propagation is generally a complex combination of small scale signal strength variations over a scale of quarter wavelength (clutter), areas of low signal (shadowing) and general signal fall off with distance.

The fall off with distance is empirically observed to be $R^{-3}$ or even faster fall off (measurements in office environments often show an index of −4 or more). In unobstructed areas free space propagation of $R^{-2}$ is expected. The variations due to clutter and shadowing will often tend to be due to obstructions close to the tag given that the reference tag can be specifically sited as far away from obstacles or scatters to maximize the predictability of the signal strength. Nevertheless the local scattering at one end will introduce uncertainties at a single point of perhaps 10 dB which corresponds to a range of uncertainty of roughly 3 to 1 for a propagation index of −3. That is, at 100 m actual range, the received power might be consistent with apparent ranges from 30 to 100 m. The position accuracy of an RSSI system is thus determined by the actual propagation conditions versus the assumed propagation conditions and the separation of the reference tags. A 100 m reference entity separation with a minimum number of reference entities will barely give 20-30 m accuracy unless other steps are taken. As such the present invention contemplates:

1. Use more reference entities spread evenly through the area. This gives some extra information which allows an asset tracking device to infer the average propagation conditions. Perhaps 5-10 reference entities would give a significant improvement in position accuracy.
2. Space the reference entities much more closely. The propagation uncertainty is then a fraction of a smaller separation. This goes together with point 1 but to get accuracy near 1 m, the spacing must go down roughly 10 m and 100 reference entitles would be needed over the 100 m by 100 m area.
3. Use some form of location survey or direct measurement of the propagation conditions of the location in question.

4. Use tracking information and knowledge of allowable pathways etc., as the reference entity is moved into place.

In some embodiments, local positioning system 111 supports a direction of signal arrival location determination scheme. In this scheme the asset tracking device measures the direction to each reference entity, or each reference entity measures the direction to the asset tracking device in question, then location of the asset tracking device can be estimated. This method of location determination has characteristics that result in poor location determination as a large power source is needed in order to resolve the direction of arrival of the signal. Additionally, the scheme is subject to error due to the well-known concept of multi-path inference.

Figure 4:
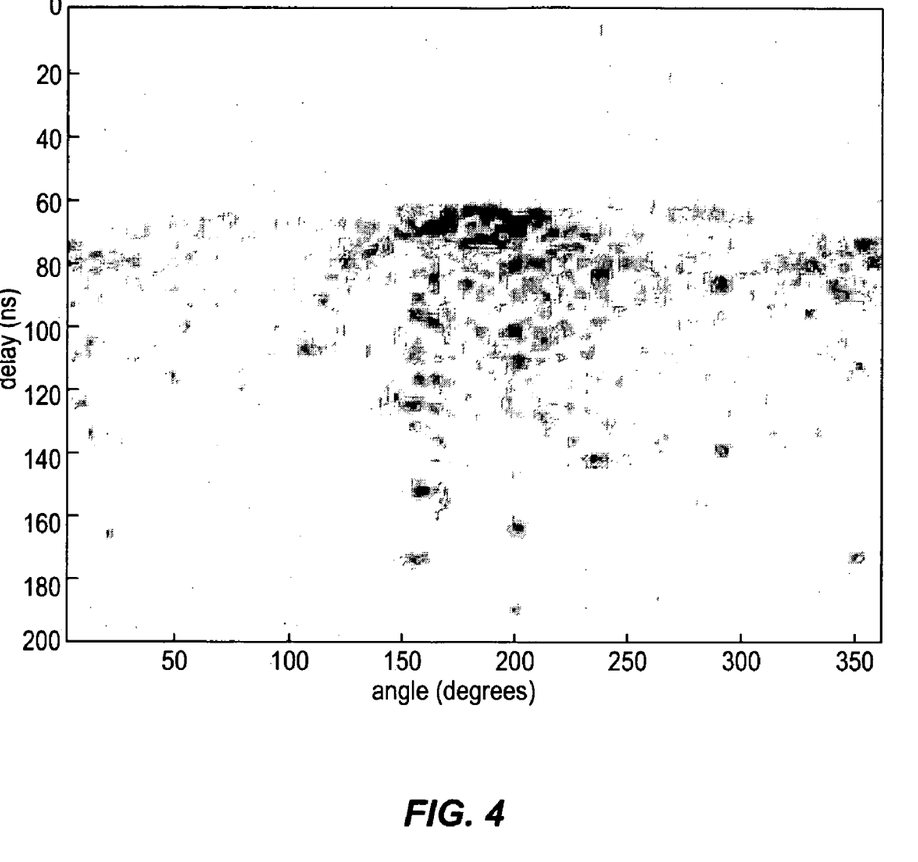
FIG. 4 shows a measured arrival time and angle of arrival of a transmitted signal in an indoor location environment.

In some embodiments, local positioning system 111 supports a time of arrival location determination scheme. FIG. 4 shows a measured arrival time and angle of arrival for an indoor environment.

FIG. 4 shows that even with significant multipath interference, the shortest time of arrival is well defined to the level of 1-2 ns, or better than 1 m. These measurements were made with broadband signals and a high gain dish antenna. The important point to note is that fundamentally the time of arrival is more robust to multipath interference and is a preferable location determination scheme if available. The shortest time is likely to be close to the direct path even when that is missing (a gazing reflection for example will be almost the same delay as the direct path).

Two broad classes of time of arrival location determination schemes are possible.

The first class is possible when the transmit time between a number of reference entities and an asset tracking device can be measured. With two reference entities, a pair of measurements defines two possible locations (actually a ring in 3 dimensions, 2 locations if we know they are on a 2D surface such as the floor). A third reference gives a unique location. This class of method is referred to as Time of Arrival (TOA).

One way of achieving TOA is to maintain synchronized clocks on all tags and reference tags. This is possible via round robin communication where each asset tracking device or reference entity takes a turn at transmitting and all asset tracking devices and reference entities listen. A calibration server is responsible for computing the clock offsets, rate offsets etc., so at some time when a location determination measurement is to be made the relative time of all the clocks can be inferred and making the calibrations available to all asset tracking devices and reference entities.

The TOA measurement could then be based on all reference tags in turn transmitting a distance probe signal with time stamp showing the time of transmission. Each asset tracking device could then infer its location by noting the receive time, transmit time, own and transmit clock offsets for each reference tag.

This scheme is characterized as being conceptually and logically inaccurate. The frequency of calibrations would also be very onerous. A clock rate error of 1 in $10^5$ would mean a time error consistent with 1 m in only 300 sec. While this rate error can itself be calibrated with successive measurements, the accuracy of that calibration and random drifts would mean very frequent calibration.

Fortunately, there is a very simple solution if a two path (i.e., tag to reference and reference to tag) measurement can be carried out. Suppose each reference tag is able to receive a TOA ranging pulse from a tag, and retransmit its own ranging pulse at a fixed time delay. The tag receives that after a time delay of twice the path delay plus some fixed retransmission delay. Note that there is no longer any requirement for accurate clock calibration for either tag or reference tag.

The second class is appropriate when the actual time of flight can not be inferred because, for example, the tag does not have a sufficiently accurate clock or does not time stamp its transmission so the receiving reference tags can only measure the differences in arrival time for the same transmission from a tag. In 2D, this reduced amount of information means a pair of reference tags can infer the position of a tag to within a hyperbola, while in 3D that expands to a hyperbolic surface. Now 3 reference tags reduce the ambiguity to 2 points and at least 4 reference tags are necessary in general. This class of method is referred to as Time Difference of Arrival (TDOA).

One way this could proceed is with each reference tag receiving ranging pulses from a tag looking to locate itself. The reference tag notes the receive time relative to its own internal clock and passes that time along with the clock offset previously calibrated. In this TDOA case, it is no longer necessary to calibrate the tag clocks. Only the reference tags need to be so calibrated. This is far less onerous (fewer tags so shorter round robin) but also the reference tags could be engineered with more accurate clocks thereby allowing less frequent calibration cycles.

There is still the problem of a requirement for a separate calibration server of the election of a head reference tag. Conceptually, the asset tracking device in accordance with the present invention is no longer master of its own location determination (although if each reference sends its result back, the tag is very nearly master).

Typically we would use some form of pseudo random noise (PRN) sequence with an average power C and a chip rate to fit in the available bandwidth. If there is a bandwidth B Hz available for ranging pulse transmissions, then it is possible to transmit a pulse p(t) which uses all of that bandwidth, $$p(t) = \text{sinc}(\pi B t)$$

so p(t) would be the best possible chip shape for accurately resolving time of arrival. This pulse is approximately 1/B 3 dB width.

The receiver correlates the received PRN sequence with the expected PRN pulse train and ideally, looks for the best fit for the time delay. If the receiver plus background noise is N and there are $N_c$ chips used to average the position, the timing uncertainty (due to the noise) is roughly, $$\tau_{rms} \approx \frac{1}{B} \sqrt{\frac{N}{C}} \frac{1}{\sqrt{N_c}}$$

If we assume 1 mW transmit power, antenna gains of 0 dB (the correct orientation cannot be counted on) and range 100 m, then at 2.4 GHz, the path loss is 101.6 dB. The noise in 60 MHz given a 4 dB noise figure is −92 dBm so C/N=−9.6 dB. A single cycle of a 511 chip PRN sequence then gives an accuracy of approximately 1.5 nsec which is approximately 0.5 m. This is effectively ten times less than the pulse width.

This factor of ten is a reasonable level of "super-resolution". If higher levels of resolution are sought, then not only does the required effective signal to noise rise but then all sorts of uncertainties such as inaccuracies in the bandpass of transmitter or receiver, IQ mismatch errors, etc., will tend to limit the accuracy.

The ANSI 371.1 physical layer would seem to be a reasonable fit with the resolution requirements. It has a 511 PRN sequence with a pulse chip rate of 30.52 MHz. This is less than the ideal achievable with a sinc-function pulse but is a reasonable practical compromise. The actual resolution versus noise equation will be slightly less advantageous. Also, some extra signal to noise margin will be necessary to account for the multipath properties of the propagation path.

The range needed is the line of sight range, which in most instances is will approximated by the first significant multipath component. In a situation where the direct path is partially blocked, that line of sight component can have reduced amplitude compared to the average power expected at that range.

How often this might happen will depend on the propagation environment the tags experience. A possible bad situation may be stacked metal-walled containers with signal access via deep corridors. A direct path may be virtually non-existent although a meaningful "Manhattan" distance may still be useful in such cases.

A margin of perhaps 10 dB will be necessary to pick up most of the loss of signal due to direct line of sight blocking.

The estimation of the first component is complicated by the need for super-resolution. The width of components as received will be the 1/B sec fundamental resolution width, but components which are possibly closer than that width will need to be resolved effectively so the first component can be detected. These issues are not present in GPS where a clean signal from the satellite is generally assumed and the super-resolution is effectively a simple interpolation to find the best fit location. The multipath case here requires the various components to be de-convolved and separated so that the first arrival of energy can be determined without large errors from later arriving components.

Figure 5:
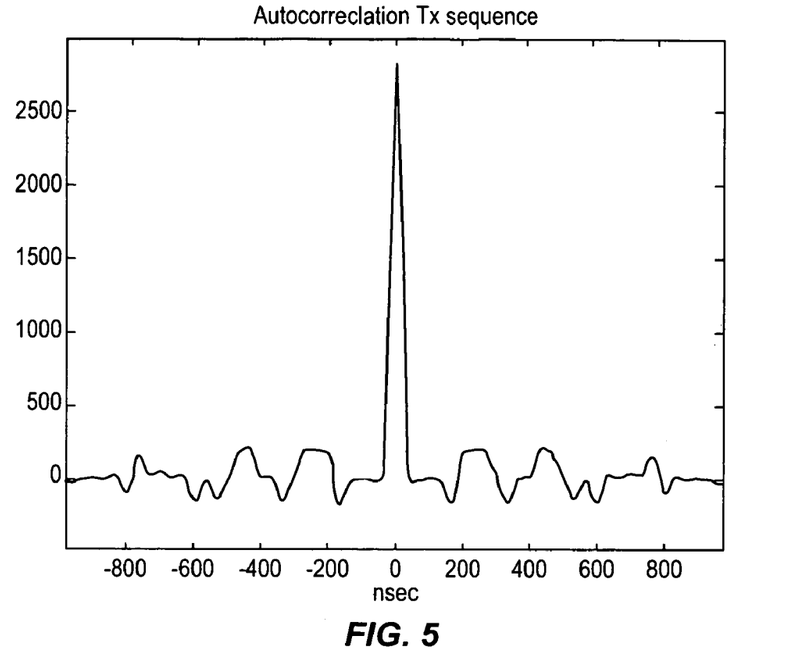
FIG. 5 shows an auto correlation function.

FIG. 5 shows an autocorrelation function of the transmitted PRN sequence as per ANSI 371.1. This is equal to the correlation of the received sequence with the transmitted sequence where the channel has only a line of sight component and no multipath.

Figure 6:
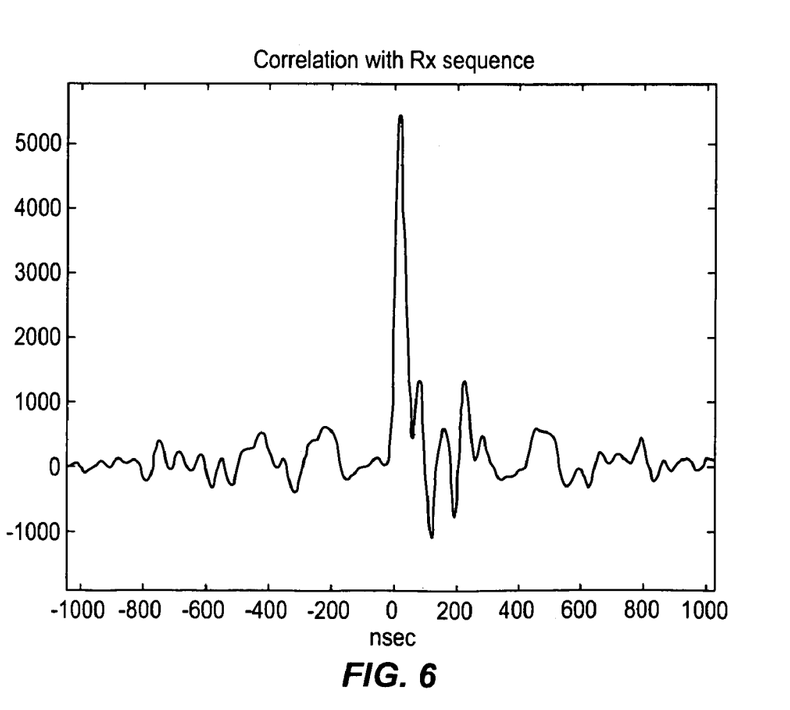
FIG. 6 shows a received signal through a multi-path channel with added receiver noise after correlation with a transmitted PRN sequence.

FIG. 6 shows the received sequence through a multipath channel with added receiver noise after correlation with the transmitted PRN sequence. Note that the LOS component at 0 nsec delay is relatively stronger than the longer delay components. This would represent a channel with modest multipath.

There are various algorithms for super-resolution time of arrival estimation including CLEAN, MUSIC, SAGE, and ESPRIT. The latter three methods seem to be increasingly commonly though of for such applications. The CLEAN algorithm is known in astronomical imaging but not well outside of that but has worked well in simulations. A relatively simple, low compute intensive algorithm is useful to run on both tag and reference tag. CLEAN is simple but is iterative and will be computationally demanding. In selecting a particular algorithm, some experimentation is helpful to determine whether the overall computational load to obtain suitable accuracy is acceptable for a given set of computational resources in the tags. It is interesting to note that MUSIC may well be a good combination of low computational burden and accuracy and further that MUSIC operates on data in the frequency domain. This may be a reason for consideration of Fourier transform methods for the multi-lagged correlation.

Figure 7:
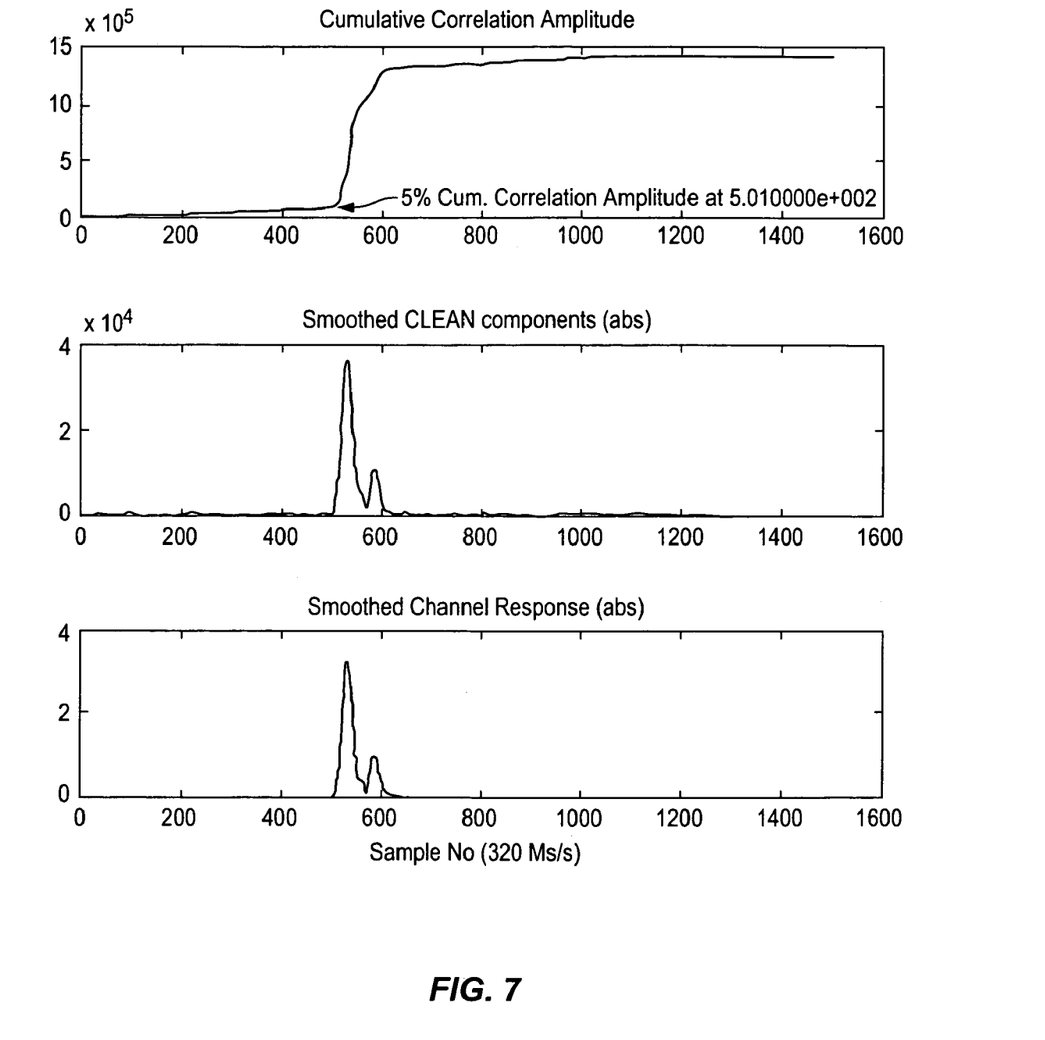
FIG. 7 shows a result of a CLEAN deconvolution algorithm applied to the correlator output as shown in FIG. 6.

FIG. 7 shows the result of the CLEAN deconvolution algorithm applied to the correlator output as shown in FIG. 6. The match of the deconvolved response and the equivalently smoothed channel response (using the central lobe of the transmit autocorrelation) is shown in the bottom two plots. The top plot shows cumulative amplitude for estimating the earliest energy arrival (500 samples is the correct answer).

Various methods in accordance with the present invention use reference tags with known position, but are otherwise initiated and managed by the tag seeking to locate itself. This is consistent with the GPS mode of operation.

One possible mode of operation is for the reference tags to continuously send a PRN sequence as in the GPS system. This could have actual position, time, and/or information modulated onto the constant transmissions in the same way. Continuous transmission is however unacceptable because some tags will be close to a reference tag and distant from other reference tags. The near-far problem means the nearby reference signal will swamp the others. Also, the nearby transmissions would interfere with 802.11 transmissions if not able to be disabled. Some form of round-robin transmission from the references could be used, although this adds complexity. The complexity associated with clock synchronization among the reference tags would also be a significant negative. Therefore some embodiments of the present invention let each tag probe the reference tags in its vicinity to determine the round trip propagation time to each, and with that information, determine its own location. This can be done without any clock synchronization and is relatively simple. One embodiment of a location determination scheme in accordance with the present invention is presented below. Note that "tag" refers to a device that would act as asset tracking device 200.

1. Tag decides to update its position or is requested to report its position.
2. Tag listens for beacon packets to determine which reference tags are within range (this may require stepping over channels unless enough can be heard on the "current channel), Each beacon would contain the coordinates (e.g., GPS coordinates) of the reference tag.
3. Tag sends an RTS packet to reserve the channel and warn that a ranging sequence is about to be transmitted.
4. Reference tag sends CTS packet to acknowledge reservation and enables its PRN correlators.
5. Tag sends N cycles of the ANSI 371.1 PRN sequence with each cycle 511 chips. N is to be determined by accuracy/range but will typically be a small number, for example, 2 to 5. The delay after receipt of CTS and transmission should be as small as practicable after correct CRC is detected (to avoid any ambiguity with PRN cycle). In typical embodiments, no modulation would be superimposed on the PRN sequence.
6. The reference tag detects the peak, and initiates the transmission of an identical PRN sequence after a delay just long enough to ensure no overlap and completion of the correlation. This will be initiated on chip clock Tclock. At the same time, the computation of the accurate received time is commenced but will not be completed until some period longer than the round trip transmission time.
7. The tag detects the reply PRN transmission peak and commences its computation of the time of arrival interpolated to a fraction of a chip time.
8. The reference tag is able, after some computation time, to determine the time it commenced its transmission Tchip and the interpolated time of arrival given as DeltaT relates to Tchip. Also needed is some turn around delay Toffset which depends on the implementation of the reference and which might be known, programmed or calibrated. This would give the offset between time of arrival estimate and the commencement of the response transmission. These 3 time measurements are returned to the tag using an 802.11 management packet (or alternatively by piggy-backing the information on the next beacon packet).

9. On receipt of the last information, the tag is able to do its own calculation of Tchip, DeltaT together with the information returned from the reference tag to get the round trip propagation time.

10. The tag updates its position after repeating this for a number of reference tags given the GPS position of each reference tag and the distance to each reference tag.

Given this sequence of events, we can determine the requirements for clock accuracy and stability, and show that there is no need for calibration of any clock offsets. That is, there is no requirement for either tags or reference tags to undergo separate clock calibration or setting. The interchange above for a single tag and a single reference with separate clocks $t_{tag}(t)$ and $t_{ref}(t)$ where t is "true" time will go as follows:

Suppose at real time t, the tag starts a PRN transmission and records the time from its clock as $t_0$.

$$t_0 = t_{tag}(t)$$

so after some time offset $Txoff_{tag}$ the signal appears at the antenna and there is a propagation delay of Tprop before the signal reaches the reference tag antenna at real time $t_1$ where, $$t_1 = t + Txoff_{tag} + Tprop$$

The reference tag then detects the time of arrival of the PRN transmission via a clock count $Tchip_{ref}$ and an interpolation Dtref which represents the reference receive time of $t_2$. So we have, $$t_2 = t_{ref}(t_1 + Troff_{ref})$$

after some processing delay which is at least as long as the length of the ranging PRN sequence, the reference tag responds by transmitting its own PRN sequence. There are various possibilities here. For example, we could rely on a fixed time delay between detecting a correlation peak and the chip clock when the response is initiated. It will be easier to not rely on a fixed delay, but simply to note the reference clock time when the response is initiated after some turn-around wait time Tturn. So the reference tag commences its response at $t_3$ where, $$t_3 = t_{ref}(t_1 + Troff_{ref} + Tturn)$$

Note that $t_2$ and $t_3$ (or $t_2$ and some difference measured in chip clock times) get communicated back to the initiating tag. Our first requirement is then that $t_3-t_2$ is sufficiently accurately able to estimate the turnaround time Tturn that was actually used. In other words, we need the reference tag clock stable over a time interval of Tturn to well within the desired timing accuracy. This would be approximately 1 nsec over a period of approximately 10 μsec (note that one 511 cycle of the approximately 30 MHz PRN sequence is 1.5 μsec). There are now delays of $Txoff_{ref}$, Tprop (channel is reciprocal), and $Troff_{tag}$ before the receiving tag is able to detect the time of arrival of the reply at $t_4$. We get finally, $$t_4 = t_{tag}(t + Txoff_{tag} + Tprop + Troff_{ref} + Tturn + Txoff_{ref} + Tprop + Troff_{tag})$$

If we then take $t_4-t_1$ and assuming the tag clock rate is accurate over the total time interval then we get, $$t_4 - t_0 = t_{tag}(t + Txoff_{tag} + Tprop + Troff_{ref} + Tturn + Txoff_{ref} + Tprop + Troff_{tag}) - t_{tag}(t) \approx Txoff_{tag} + Tprop + Troff_{ref} + Tturn + Txoff_{ref} + Tprop + Troff_{tag}$$

Given we have the estimate of Tturn sent back from the reference tag and given that the delay terms Txoff, Troff include a small analog delay (RF delays of several hundred picoseconds) which can be estimated and a probably much larger digital delay which should be known with certainty, the propagation time Tprop can be accurately estimated.

The tag clock now must have better than 1 nsec rate accuracy over the entire measurement interval which is dominated by the reference turn around interval Tturn. This means both tag and reference need clock stability of 1 nsec in 20 μsec, or 5 parts in $10^5$ over 20 μsec. The actual clock offsets are not needed, and no clock calibration step is necessary for the location.

In some embodiments, the PRN code is sent in the place where an 802.11 data payload might otherwise be. By hiding the PRN code in this way, the other 802.11 devices back off and allow the PRN code to be transmitted. Such embodiments ensure that the PRN code does not interfere with other 802.11 transactions. Similarly, this ensures that 802.11 transactions do not interfere with the PRN code transmission.

It is noted that, when GPS-like data is transmitted over the 802.11 2.4 GHz band, data can be encoded on top of such transmissions. This arrangement allows for sending small amount of data over relatively long distances, for example a few miles versus a few hundred feet using conventional 802.11. In this way, all containers on a container ship that include asset tracking devices in accordance with the present invention can be "seen" from a single point, such as the bridge of the ship.

CONCLUSION

Described herein are methods and systems for determining the location of asset tracking devices when GPS signals are obstructed by determining which one or more local location determination schemes are available, selecting at least one of the local location determination schemes, and communicating with a plurality of the reference tags of the selected local location determination scheme, those reference tags having known locations, and finally determining the distances of the asset tracking from each of several reference tags, and from that information computing the actual location of the asset tracking device.

It is to be understood that the present invention is not limited to the embodiments described above, but encompasses any and all embodiments within the scope of the subjoined claims and their equivalents.

What is claimed is:

1. A method comprising:
    searching, by an asset tracking device, for available location determination schemes;
    selecting one of the available location determination schemes; and
    determining coordinates of the position of the asset tracking device using the selected location determination scheme by listening, by the asset tracking device, for beacon packets transmitted by one or more reference tags to determine which reference tags are within range, each beacon packet including the coordinates of the position of the transmitting reference tag.

2. The method of claim 1, further comprising transmitting a location message, the location message including the coordinates of the location of the asset tracking device.

3. The method of claim 2, wherein the location message includes an identification of the selected location determination scheme.

4. The method of claim 2, further comprising:
receiving, at the asset tracking device, a request for a location message, and
wherein the location message is transmitted in response to the request.

5. The method of claim 1, wherein the selected location determination scheme is a time of arrival scheme.

6. The method of claim 1, wherein the selected location determination scheme is a time difference of arrival scheme.

7. The method of claim 1, wherein the selected location determination scheme is a received signal strength indicator scheme.

8. The method of claim 1, further comprising:
transmitting, from the asset tracking device, an RTS packet;
receiving, at the asset tracking device, a CTS packet;
transmitting, from the asset tracking device, a first PRN sequence;
receiving, at the asset tracking device, a second PRN sequence; and
determining, subsequent to receiving the second PRN sequence, the time or arrival of the second PRN sequence;
wherein the first PRN sequence and the second PRN sequence are identical, and
wherein transmissions are in an 802.11 protocol, and the first and second PRN sequences are transmitted in place of an 802.11 payload.

9. The method of claim 1 further comprising receiving, at the asset tracking device, timing information from the reference tag.

10. The method of claim 1, further comprising determining, by the asset tracking device, whether it is able to determine its position coordinates based upon GPS signals, and wherein searching is performed subsequent to a determination that the asset tracking device is unable to determine its position coordinates based upon GPS signals.

11. The method of claim 1, further comprising the asset tracking device transitioning from a sleep state to a wake state at predetermined time intervals.

12. The method of claim 1, wherein the asset tracking device is an RFID tag.

13. The method of claim 12, wherein the asset tracking device is attached to an asset to be tracked.

14. The method of claim 2, wherein transmitting a location message comprises transmitting the location message through the Internet.

15. A system, comprising:
at least one asset tracking device, the asset tracking device including a communications module, a processing and storage module coupled to the communications module, and a location module coupled to the processing and storage module;
a network access point, wirelessly coupled to the at least one asset tracking device; and
a local positioning system comprising a plurality of reference tags, each of the reference tags having its known position coordinates stored therein, the reference tags wirelessly coupled to receive signals transmitted from the at least one asset tracking device, and to transmit signals to the at least one asset tracking device;
wherein the at least one asset tracking device is operable to determine that its location module is unable to determine position coordinates from GPS signals, is further operable to search for one or more reference tags of the local positioning system, to communicate with the local positioning system so as to gather the information necessary to compute its position coordinates; and
wherein the at least one asset tracking device is an RFID tag attached to an item to be tracked.

16. An asset tracking device comprising:
a communications module to receive position signals from transmitters associated with a plurality of available location determination schemes;
a processor coupled to the communications module to select one of the available location determination schemes; and
a location module coupled to the processor module to determine coordinates of the position of the asset tracking device using the selected location determination scheme by listening for beacon packets transmitted by one or more reference tags to determine which reference tags are within range, each beacon packet including the coordinates of the position of the transmitting reference tag,
wherein the communications module is further to transmit a location message based on the selected location determination scheme.

17. The asset tracking device of claim 16, wherein the communications module includes a GPS receiver and a wireless local area network transceiver.

18. The asset tracking device of claim 16, wherein the message includes an identification of the selected location determination scheme.

19. The asset tracking device of claim 16, wherein selecting one of the available location determination schemes comprises determining first whether it is able to determine its position coordinates based upon OPS signals and, if not, then selecting another scheme.

20. The asset tracking device of claim 16, wherein the device is attached to a movable asset and wherein the communications module is a wireless communications is module.

21. The system of claim 15, wherein the at least one asset tracking device transmits a location message included its computed position to a tracking entity through the Internet.

22. The system of claim 15, further comprising receiving, at the asset tracking device, timing information from at least one reference tag of the local positioning system.

* * * * *